(12) United States Patent
Chen

(10) Patent No.: US 10,241,057 B2
(45) Date of Patent: Mar. 26, 2019

(54) OPTICAL INSPECTING APPARATUS WITH AN OPTICAL SCREENING DEVICE

(71) Applicant: STEK CO., LTD, Taichung (TW)

(72) Inventor: Ming-Sheng Chen, Taichung (TW)

(73) Assignee: STEK CO., LTD, Taichung (TW)

( * ) Notice: Subject to any disclaimer, the term of this patent is extended or adjusted under 35 U.S.C. 154(b) by 0 days.

(21) Appl. No.: 15/697,204

(22) Filed: Sep. 6, 2017

(65) Prior Publication Data

US 2018/0238812 A1  Aug. 23, 2018

(51) Int. Cl.
| | | |
|---|---|---|
| G01N 21/00 | (2006.01) | |
| G01N 21/88 | (2006.01) | |
| G01N 21/90 | (2006.01) | |
| G06T 7/00 | (2017.01) | |
| G01N 21/89 | (2006.01) | |
| G01N 21/956 | (2006.01) | |

(52) U.S. Cl.
CPC ..... G01N 21/8851 (2013.01); G01N 21/8916 (2013.01); G01N 21/9009 (2013.01); G01N 21/956 (2013.01); G06T 7/001 (2013.01)

(58) Field of Classification Search
CPC .... G01N 21/55; G01N 21/958; G01N 21/896; G01N 21/94; G01N 2021/9513; G01N 21/8851; G01N 21/9009; G01N 21/8916; G01N 21/956; G06T 7/001
USPC ...................... 356/237.1–237.5, 239.1, 239.2
See application file for complete search history.

(56) References Cited

U.S. PATENT DOCUMENTS

| | | | | |
|---|---|---|---|---|
| 2,215,211 | A * | 9/1940 | Devol | G01N 21/55 250/222.1 |
| 3,857,637 | A * | 12/1974 | Obenreder | G01B 11/303 356/239.7 |
| 5,298,974 | A * | 3/1994 | Chandley | G01B 11/303 250/559.06 |
| 6,166,808 | A * | 12/2000 | Greve | G01B 11/06 250/548 |
| 6,414,751 | B1 * | 7/2002 | Kurogama | G01N 21/55 356/237.1 |
| 7,477,388 | B1 * | 1/2009 | Liphardt | G01N 21/211 356/364 |
| 2016/0025618 | A1 * | 1/2016 | Ryu | G01N 21/211 356/369 |
| 2018/0238813 | A1 * | 8/2018 | Chen | G01N 21/94 |

* cited by examiner

*Primary Examiner* — Hoa Pham

(57) ABSTRACT

An optical screening device includes a box and a light source. The box includes two chambers. The first chamber includes an incident passageway made with an exit. The second chamber includes a reflection passageway made with an entrance and an exit. The light source is inserted in the first chamber and adapted for casting incident light onto a first face of an inspected object located out of the box through the exit of the incident passageway so that primary reflected light goes into the second chamber from the first face of the inspected object via the entrance of the reflection passageway and goes out of the second chamber through the exit of the reflection passageway. The entrance of the reflection passageway is made with small width to allow only the primary reflected light to enter the second chamber.

11 Claims, 6 Drawing Sheets

OPTICAL INSPECTING APPARATUS WITH AN OPTICAL SCREENING DEVICE

BACKGROUND OF INVENTION

1. Field of Invention

The present invention relates to optical inspection and, more particularly, to an optical inspecting apparatus that receives only primary reflected light from a plate.

2. Related Prior Art

Referring to FIG. 1, a conventional mask-inspecting apparatus is equipped with an optical inspecting apparatus that includes a light source L and a photo sensor C such as a charge-coupled device ("CCD") or a complementary metal-oxide semiconductor ("CMOS"). The light source L casts light (the "incident light") Lo onto a face P1 of a transparent plate P. The face P1 reflects the incident light Lo and transmits reflected light Lr (the "primary reflected light Lr1") to the photo sensor C. There are an incident angle $\theta 1$ between the incident light Lo and a normal line of the face P1 and a reflection angle $\theta 2$ between the primary reflected light Lr1 and the normal line of the face P1. The incident angle $\theta 1$ is identical to the reflection angle $\theta 2$. The photo sensor C receives and processes the primary reflected light Lr1 from the face P1 to detect any stain on the face P1.

However, according to Snell's Law, some of the incident light Lo (the "light Lc") goes through the face P1 and gets refracted, and then reaches another face P2 of the transparent plate P. Some of the light Lc gets reflected from the face P2. Some of the light reflected from the face P2 gets refracted by the face P1 and becomes secondary reflected light Lr2. Such a process continues until the light is too weak to be detected by the photo sensor C.

Referring to FIG. 2, there are superimposed images because the photo sensor C receives the secondary reflected light Lr2 or any other light reflected from the face P2 and refracted by the face P1 in addition to the primary reflected light Lr1. For example, there is a stain A on the face P1, and there is a stain B on the face P2. The photo sensor C detects both of the stains A and B. Hence, the stain A on the face P1 cannot be detected effectively. In addition, it is difficult to determine the focal length since the plate P is a transparent element without any reference point, and this further reduces the efficiency of the inspection.

To overcome the above-mentioned problem, there has been an attempt to enlarge the scanned range and delete the superimposed images by providing a linear light source to cast light onto the transparent plate P, with the incident angle $\theta 1$ set to be about 85 degrees, i.e., the incident light Lo is close to the face P1. This approach keeps the photo sensor C from any secondary reflected light. However, the shadow of a stain is longer as the incident angle $\theta 1$ is smaller, and a long shadow renders it difficult to determine the size of the stain. Moreover, it is difficult for the incident light to produce an image of a planar stain such as atomization, grease or fingerprint if the incident angle is small.

To solve the foregoing problem, there has been an attempt to provide the optical inspecting apparatus with two light sources. This approach solves the problem of misjudging of the size of a stain. However, this inevitably increases the cost of the optical inspecting apparatus.

The present invention is therefore intended to obviate or at least alleviate the problems encountered in prior art.

SUMMARY OF INVENTION

It is an objective of the present invention to provide an optical inspecting apparatus with an optical screening device.

To achieve the foregoing objective, the optical screening device includes a box and a light source. The box includes two chambers. The first chamber includes an incident passageway made with an exit. The second chamber includes a reflection passageway made with an entrance and an exit. The light source is inserted in the first chamber and adapted for casting incident light onto a first face of an inspected object located out of the box through the exit of the incident passageway so that primary reflected light goes into the second chamber from the first face of the inspected object via the entrance of the reflection passageway and goes out of the second chamber through the exit of the reflection passageway. The entrance of the reflection passageway is made with small width to allow only the primary reflected light to enter the second chamber.

It is another objective of the present invention to provide an effective inspecting apparatus.

To achieve the foregoing objective, the optical inspecting apparatus includes a light source, a photo sensor and an optical screening device. The light source casts incident light onto a face of an inspected object so that the face of the inspected object provides primary reflected light and at least secondary reflected light. The optical screening device allows the primary reflected light to reach the photo sensor but blocks the secondary reflected light.

Other objectives, advantages and features of the present invention will be apparent from the following description referring to the attached drawings.

BRIEF DESCRIPTION OF DRAWINGS

The present invention will be described via detailed illustration of embodiments in view of the prior art referring to the drawings wherein.

DETAILED DESCRIPTION OF EMBODIMENTS

Figure 1:
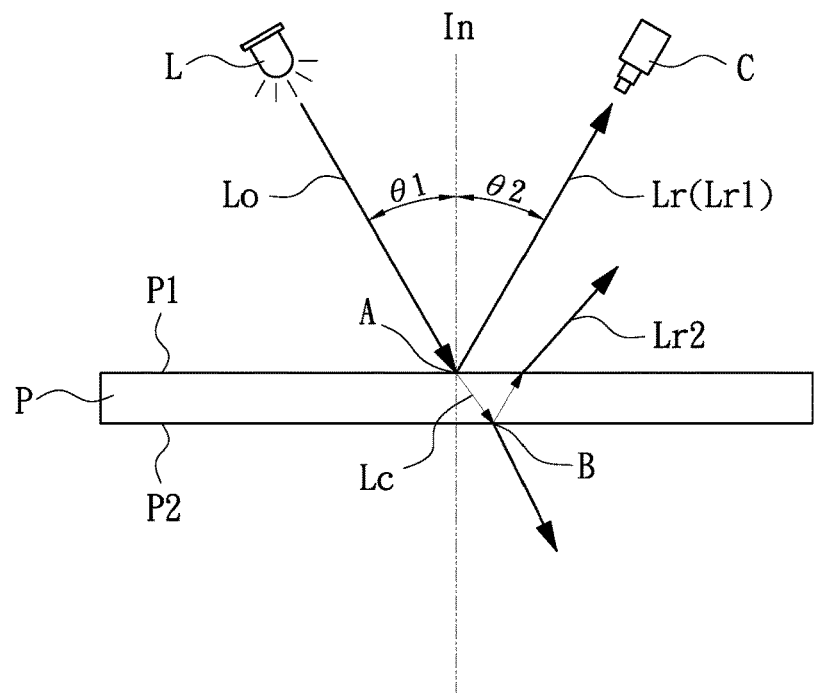
FIG. 1 is a front view of a conventional optical inspecting apparatus.
Figure 2:
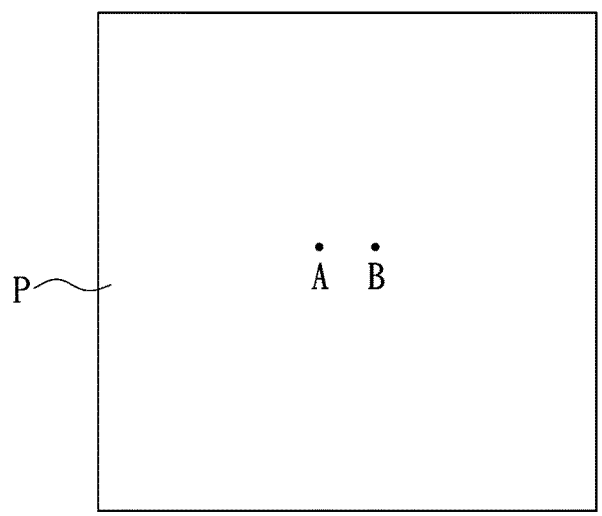
FIG. 2 is an image of a transparent plate obtained by the conventional optical inspecting apparatus shown in FIG. 1.
Figure 3:
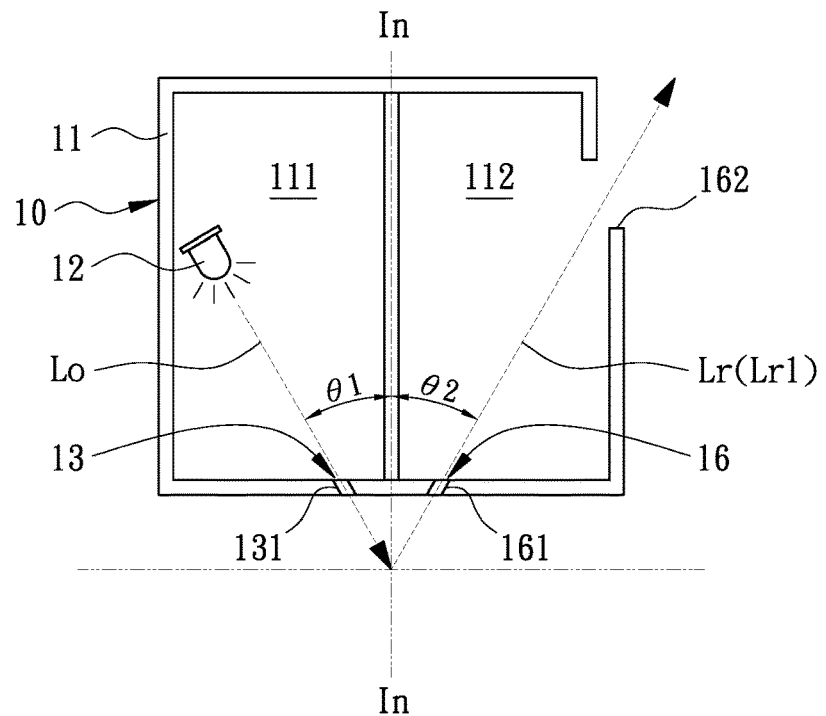
FIG. 3 is a front view of an optical inspecting apparatus according to a first embodiment of the present invention.

Referring to FIG. 3, an object 60 for use in a semiconductor device, a panel or a package can be inspected by an optical apparatus that includes an optical screening device 10 according to a first embodiment of the present invention. The inspected object 60 can be a mask, a substrate or a panel made of glass or quartz. The optical screening device 10 includes a box 11 and a light source 12.

The box 11 includes two chambers 111 and 112, an incident passageway 13 in the chamber 111, and a reflection passageway 16 in the chamber 112. The incident passageway 13 includes an exit 131 in communication with the chamber 111. The width of the exit 131 of the incident passageway 13 is preferably 0.1 to 0.5 mm. The reflection passageway 16 includes an entrance 161 in communication with the chamber 112 and an exit 162 in communication with the chamber 112. The entrance 161 of the reflection passageway 16 is preferably made with width of 0.1 to 0.5 mm. The exit 162 of the reflection passageway 16 is preferably made with width of 0.2 to 20 mm.

The optical screening device 10 includes a single box 11 that includes two chambers 111 and 112 in the preferred embodiment. However, the optical screening device 10 can include two boxes, with each of the boxes including a single chamber in another embodiment.

The light source 12 can be a halogen lamp, and LED lamp, a high-frequency fluorescent lamp, a metal lamp, a xenon lamp or a laser lamp that emits visible or invisible light that can be detected by a charge-coupled device ("CCD") or a complementary metal-oxide semiconductor ("CMOS"). The light source 12 is inserted in the chamber 111.

The light source 12 casts light. Some of the light cast from the light source goes out of the chamber 111 through the exit 131 of the incident passageway 13 and will be referred to as the "incident light Lo" in the following description. Then, the incident light Lo reaches a first face of the inspected object 60 at an incident angle θ1 measured from a normal line of the first face of the inspected object 60. The incident angle θ1 is preferably 15 to 45 degrees and, more preferably, 27 to 33 degrees. The width of the exit 131 of the incident passageway 13 is 0.1 to 0.5 mm.

The first face of the inspected object 60 reflects some of the incident light Lo and hence provides primary reflected light Lr1 at a reflection angle θ2 identical to the incident angle θ1. The primary reflected light Lr1 enters the chamber 112 via the entrance 161 of the reflection passageway 16. Where the inspected object 60 is a transparent plate, the entrance 161 of the reflection passageway 16 is only wide enough to let the primary reflected light Lr1 into the chamber 112 from the first face of the transparent plate P. The box 11 blocks secondary reflected light Lr2 or any other light reflected from a second face of the inspected object 60 and refracted by the first face of the inspected object 60. The width of the exit 162 of the reflection passageway 16 is made according to the width and position of the entrance 161. Preferably, the width of the exit 162 of the reflection passageway 16 is made larger than that of the entrance 161.

Figure 4:
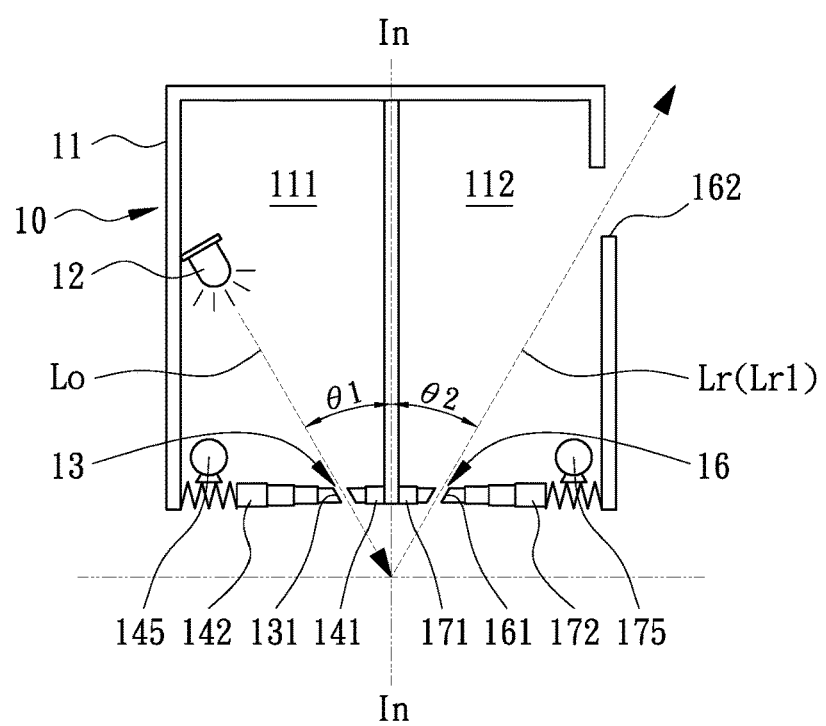
FIG. 4 is a front view of an optical inspecting apparatus according to a second embodiment of the present invention.

Referring to FIG. 4, there is an optical screening device 10 according to a second embodiment of the present invention. The second embodiment is identical to the first embodiment except for including two adjusting units in addition. The first adjusting unit is located in the chamber 111 to control the width and position of the exit 131. The second adjusting unit is located in the chamber 112 to control the width and position of the entrance 161.

The first adjusting unit includes two extensible visors 141 and 142 and at least one driving element 145. Each of the extensible visors 141 and 142 is movable by the driving element 145. Thus, the position and width of the exit 131 of the incident passageway 13 are adjustable. Hence, the incident angle θ1 can be adjusted by changing the position of the exit 131 of the incident passageway 13. The position of the exit 131 of the incident passageway 13 is set so that the incident angle θ1 is 15 to 45 degrees. The width of the incident light Lo can be adjusted by changing the width of the exit 131 of the incident passageway 13. The width of the exit 131 of the incident passageway 13 is preferably 0.1 to 0.5 mm.

Similarly, the second adjusting unit includes two extensible visors 171 and 172 and at least one driving element 175. Each of the extensible visors 171 and 172 is movable by the driving element 175. Thus, the position and width of the entrance 161 of the reflection passageway 16 are adjustable. Hence, the reflection angle θ2 can be adjusted by changing the position of the entrance 161 of the reflection passageway 16. The position of the entrance 161 of the reflection passageway 16 is set so that the reflection angle θ2 is 15 to 45 degrees. The width of the primary reflected light Lr1 can be adjusted by changing the width of the entrance 161 of the reflection passageway 16. The width of the entrance 161 of the reflection passageway 16 is preferably 0.1 to 0.5 mm.

Figure 5:
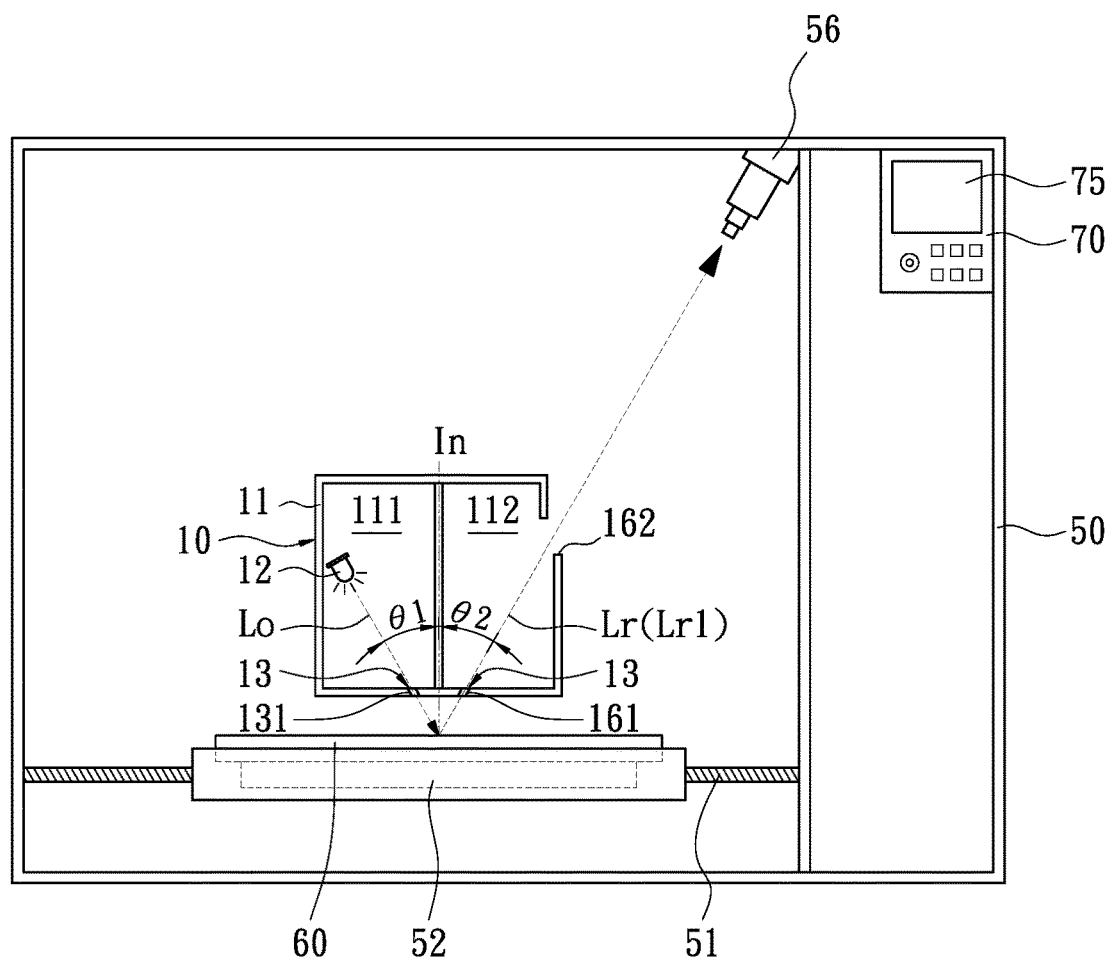
FIG. 5 is a front view of a machine including the optical inspecting apparatus shown in FIG. 3.

Referring to FIG. 5, an optical inspecting machine includes a frame 50, a worktable 51 supported on the frame 50, a carrier 52 movable on the worktable 51, and a single optical inspecting apparatus 55 located above the worktable 51. An inspected object 60 is laid on the carrier 52. Only an upper face of the inspected object 60 is inspected at a time.

The optical inspecting apparatus 55 includes an optical screening device 10 and a photo sensor 56. The photo sensor 56 is a charge-coupled device ("CCD") or a complementary metal-oxide semiconductor ("CMOS") element for example. There is an incident angle θ1 between the incident light cast from the light source 12 of the optical screening device 10 and a normal line of the upper face of the inspected object 60. There is a reflection angle θ2 of the reflected light received by the photo sensor 56 and the normal line. The incident angle θ1 is identical to the reflection angle θ2. The light source 12 and the photo sensor 56 are electrically connected to a processing unit 70 for calculating, comparing and analyzing data. The processing unit 70 includes a display 75. The processing unit 70 is used to control the intensity of the incident light cast from the light source 12 and show an image of the inspected object 60 based on the reflected light received by the photo sensor 56 on the display 75. Thus, the position, size, shape and type of any stain on the inspected object 60 can be determined.

Figure 6:
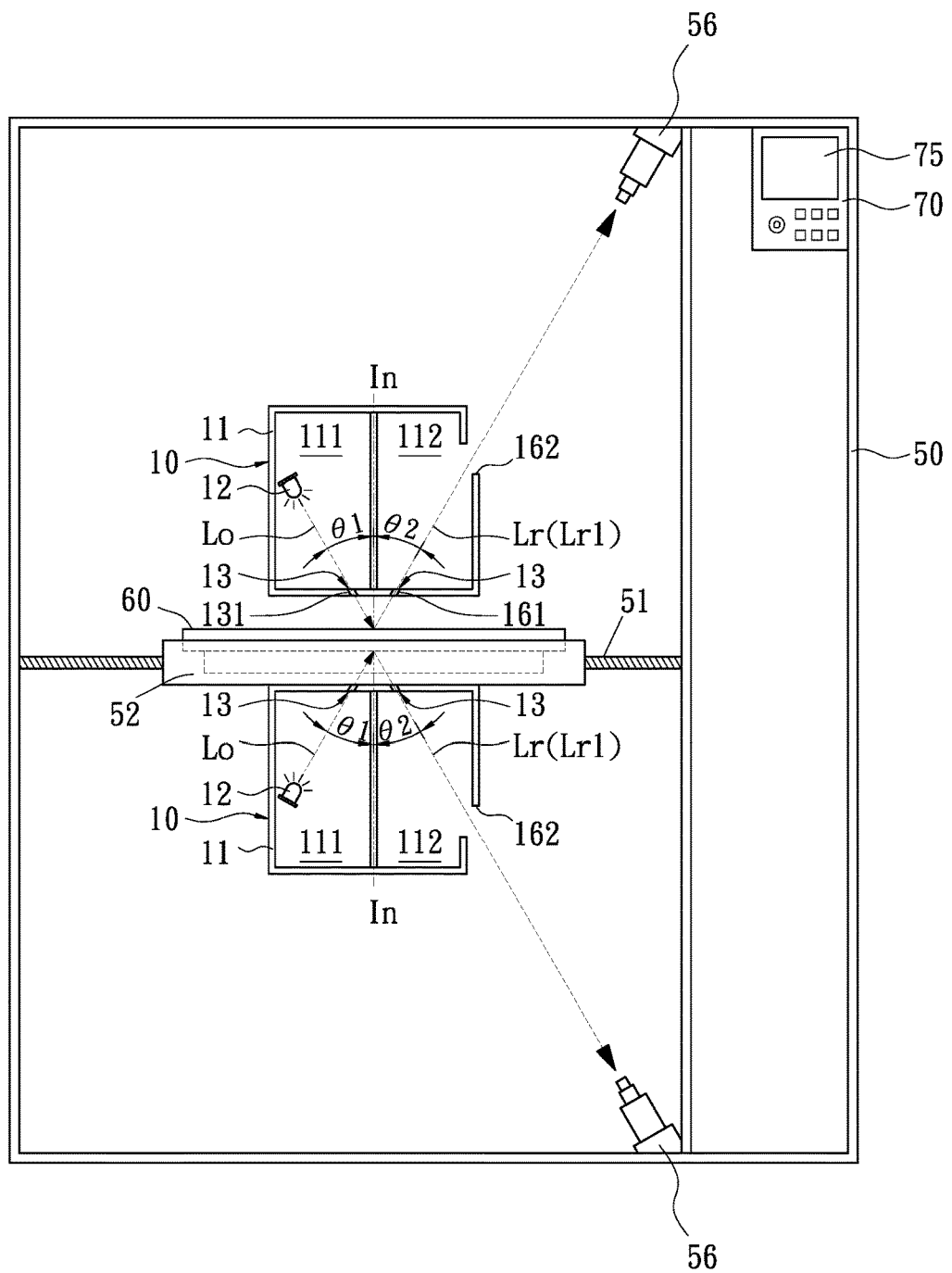
FIG. 6 is a front view of another machine including two optical inspecting apparatuses as shown in FIG. 3.

Referring to FIG. 6, an optical inspecting machine can be equipped with two optical inspecting apparatuses 55. One of the optical inspecting apparatuses 55 is located above the worktable 51 while the other optical inspecting apparatus 55 is located below the worktable 51. Thus, upper and lower faces of the inspected object 60 are inspected at a time.

Figure 7:
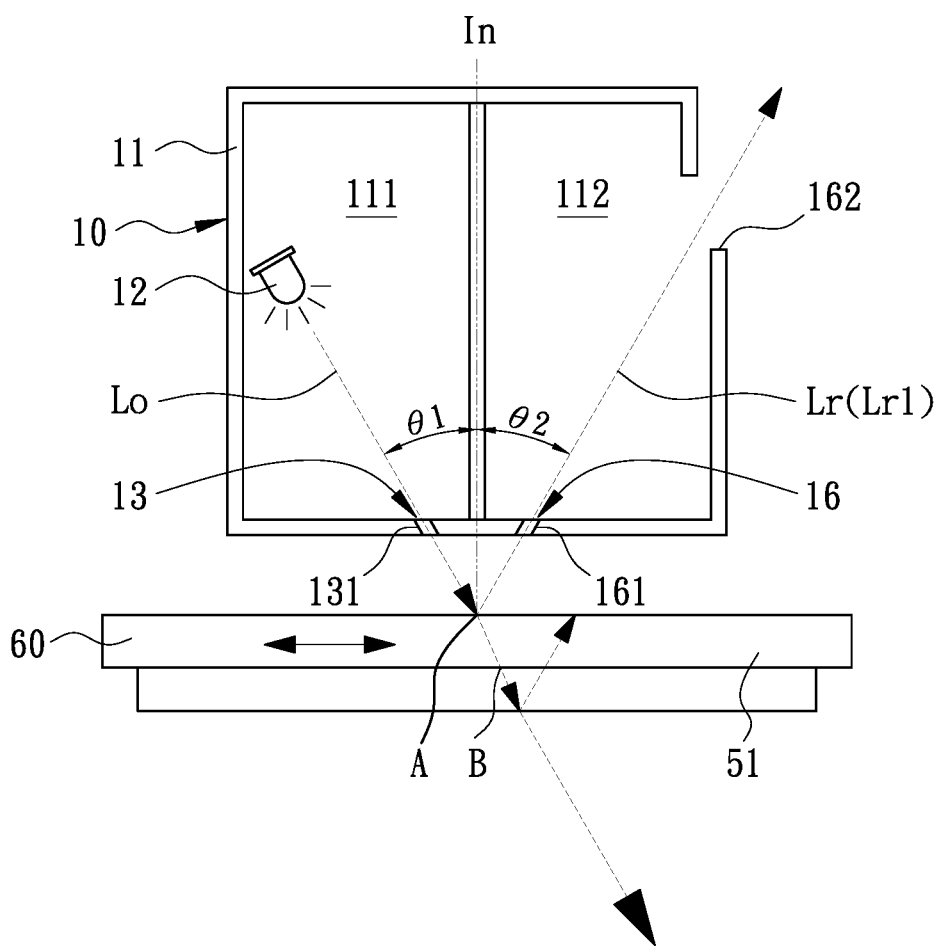
FIG. 7 is a front view of a transparent plate inspected by the optical inspecting apparatus shown in FIG. 3.
Figure 8:
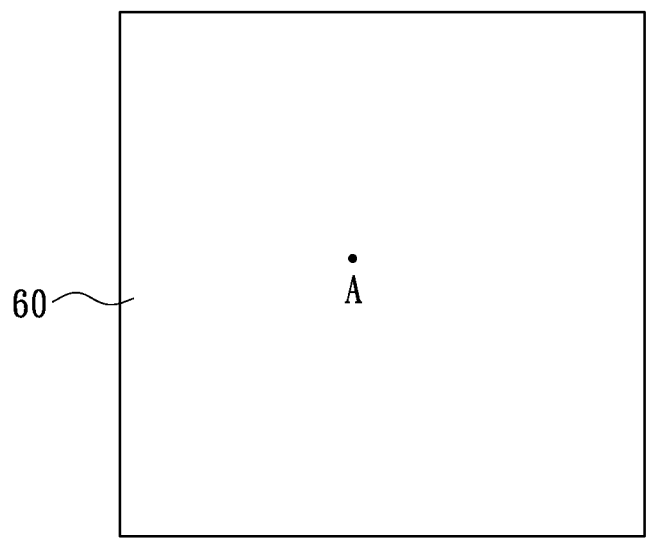
FIG. 8 is an image of the transparent plate obtained by the optical inspecting apparatus shown in FIG. 7.

Referring to FIGS. 5, 7 and 8, the optical inspecting machine is used to detect any stain on the upper face of the inspected object 60. As mentioned above, the inspected object 60 is located on the carrier 52 of the frame 50 so that the carrier 52 is movable on the worktable 51. The processing unit 70 is used to make the light source 12 of the optical screening device 10 to cast light. Some of the light goes out of the chamber 111 of the box 11 through the exit 131 of the incident passageway 13 of and becomes the incident light Lo cast onto the upper face of the inspected object 60. Some of the incident light Lo gets reflected from the upper face of the inspected object 60 and becomes the primary reflected light Lr1. The incident angle θ1 is identical to the reflection angle θ2. The primary reflected light Lr1 enters the box 11 via the entrance 161 of the reflection passageway 16 and leaves the box 11 through the exit 162 of the reflection passageway 16 of the chamber 112. The photo sensor 56 receives the primary reflected light Lr1. Due to the limited width of the entrance 161 of the reflection passageway 16, the chamber 112 of the box 11 is kept clear of the secondary reflected light Lr2 and any other light reflected from the lower face of the inspected object 60 and refracted by the upper face of the inspected object 60. Thus, the secondary reflected light Lr2 and any other light reflected from the lower face of the inspected object 60 and refracted by the upper face of the inspected object 60 is blocked. Only a stain A on the upper face of the inspected object 60 is shown on the image of the inspected object 60 produced by the photo sensor 56. No stain on the lower face of the inspected object 60 is shown on the image of the inspected object 60 produced by the photo sensor 56.

The photo sensor 56 receives the primary reflected light Lr1 from every region of the upper face of the inspected object 60 while the carrier 52 continuously moves the inspected object 60. All of the energy of the primary reflected light Lr1 is converted into charge. The stronger the primary reflected light Lr1 is, the larger the charge is. The intensity of the primary reflected light Lr1 is determined according to the quantity of the charge. The intensity of the primary reflected light Lr1 from a region of the upper face of the inspected object 60 is relatively low if there is a stain on the region. Thus, the intensity of the primary reflected light Lr1 sent to the photo sensor 56 from all regions of the upper face of the inspected object 60 is processed to provide an image of the entire upper face of the inspected object 60 to determine the position, size, shape and type of any stain on the upper face of the inspected object 60.

As discussed above, with the incident passageway 13 and the reflection passageway 16 of the optical screening device 10, only the primary reflected light Lr1 from the upper face of the inspected object 60 reaches the reflected from the lower face of the inspected object 60 and refracted by the upper face of the inspected object 60 is blocked. Thus, no stain on the lower face of the inspected object 60 is shown on the image of the upper face of the inspected object 60. Hence, the position, size, shape, position and type of any stain on the upper face of the inspected object 60 can be effectively determined. Moreover, planar contaminant such as atomization, grease, fingerprint or cracks can be detected.

The present invention has been described via illustration of the embodiments. Those skilled in the art can derive variations from the embodiments without departing from the scope of the present invention. Therefore, the embodiments shall not limit the scope of the present invention defined in the claims.

The invention claimed is:

1. An optical screening device comprising:
   a box comprising:
      a first chamber comprising an incident passageway made with an exit; and
      a second chamber comprising a reflection passageway made with an entrance and an exit;
   a light source inserted in the first chamber and adapted for casting incident light onto a face of an inspected object located out of the box through the exit of the incident passageway so that primary reflected light goes into the second chamber from the face of the inspected object via the entrance of the reflection passageway and goes out of the second chamber through the exit of the reflection passageway, wherein the entrance of the reflection passageway is made with small width to allow only the primary reflected light to enter the second chamber; and
   an adjusting unit provided in the first chamber and operable to adjust the position and width of the exit of the incident passageway.

2. The optical screening device according to claim 1, wherein the light source is selected from the group consisting of a halogen lamp, an LED lamp, a high-frequency fluorescent lamp, a metal lamp, a xenon lamp or a laser lamp.

3. The optical screening device according to claim 1, wherein the incident passageway is arranged so that the incident light teaches the face of the inspected object at an incident angle of 15 to 45 degrees.

4. The optical screening device according to claim 1, wherein the adjusting unit comprises two extensible visors.

5. The optical screening device according to claim 4, wherein the adjusting unit further comprises a motor for driving the extensible visors.

6. The optical method according to claim 1, wherein the exit of the incident passageway is made with width of 0.1 to 0.5 mm.

7. The optical screening device according to claim 1, wherein the entrance of the reflection passageway is made with width of 0.1 to 0.5 mm.

8. The optical screening device according to claim 1, wherein the exit of the reflection passageway is made with width of 0.2 to 20 mm.

9. An optical screening device comprising:
   a box comprising:
      a first chamber comprising an incident passageway made with an exit; and
      a second chamber comprising a reflection passageway made with an entrance and an exit;
   a light source inserted in the first chamber and adapted for casting incident light onto a face of an inspected object located out of the box through the exit of the incident passageway so that primary reflected light goes into the second chamber from the face of the inspected object via the entrance of the reflection passageway and goes out of the second chamber through the exit of the reflection passageway, wherein the entrance of the reflection passageway is made with small width to allow only the primary reflected light to enter the second chamber; and
   an adjusting unit provided in the second chamber and operable to adjust the position and width of the entrance of the reflection passageway.

10. The optical screening device according to claim 9, wherein the adjusting unit comprises two extensible visors.

11. The optical screening device according to claim 10, wherein the adjusting unit further comprises a motor for driving the extensible visors.

\* \* \* \* \*